United States Patent [19]

Izumi

[11] Patent Number: 5,097,827

[45] Date of Patent: Mar. 24, 1992

[54] HOLDER FOR MEDICAL TUBING

[75] Inventor: John Izumi, Glen Ellyn, Ill.

[73] Assignee: DDI Industries, Inc., Bedford Park, Ill.

[21] Appl. No.: 673,379

[22] Filed: Mar. 22, 1991

[51] Int. Cl.[5] .................. A61M 15/08; A62B 7/00
[52] U.S. Cl. .................. 128/207.18; 128/DIG. 26; 128/911; 128/912; 128/207.13; 128/200.26; 128/204.12
[58] Field of Search ............... 128/911, 912, DIG. 26, 128/206.18, 207.13, 207.18, 200.24, 200.26, 204.12; 606/198, 199

[56] References Cited

U.S. PATENT DOCUMENTS

| | | | |
|---|---|---|---|
| 3,203,421 | 8/1965 | Bialick | 128/DIG. 25 |
| 3,915,173 | 10/1975 | Brekke | 128/207.18 |
| 4,336,806 | 6/1982 | Eldridge, Jr. | 128/348 |
| 4,648,398 | 3/1987 | Agdanowski et al. | 128/207.18 |
| 4,683,882 | 8/1987 | Laird | 128/207.17 |
| 4,707,906 | 11/1987 | Posey | 29/453 |
| 4,757,813 | 7/1988 | Haydu | 128/201.26 |
| 4,932,943 | 6/1990 | Nowak | 128/DIG. 26 |
| 4,986,815 | 1/1991 | Schneider | 128/DIG. 26 |

Primary Examiner—Edgar S. Burr
Assistant Examiner—Lisa E. Malvaso
Attorney, Agent, or Firm—Marshall, O'Toole, Gerstein, Murray & Bicknell

[57] ABSTRACT

A medical tube holder for attachment to a patient's nose septum for holding medical tubing inserted into the patient's nose. The tube holder includes opposite upstanding clamp arms defining an acute included angle therebetween for insertion into the nostril and thereby into clamp engagement on opposite sides of the patient's septum. One of the nasal clamp arms includes a tube holder section for substantially surrounding and maintaining medical tubing in position. A thumbscrew adjusts the distance between the upstanding clamp arms and therefore the clamping pressure on the septum. A rotating screw in another embodiment is fixed to one clamp arm and threadably mounted on another clamp arm to provide threadable adjustment. A locking pin and detent configuration in a further embodiment enables adjustment of the clamp arms between preset positions. An integral unit in a still further embodiment with two opposing upstanding clamp arms set at an optimum acute included angle therebetween.

20 Claims, 2 Drawing Sheets

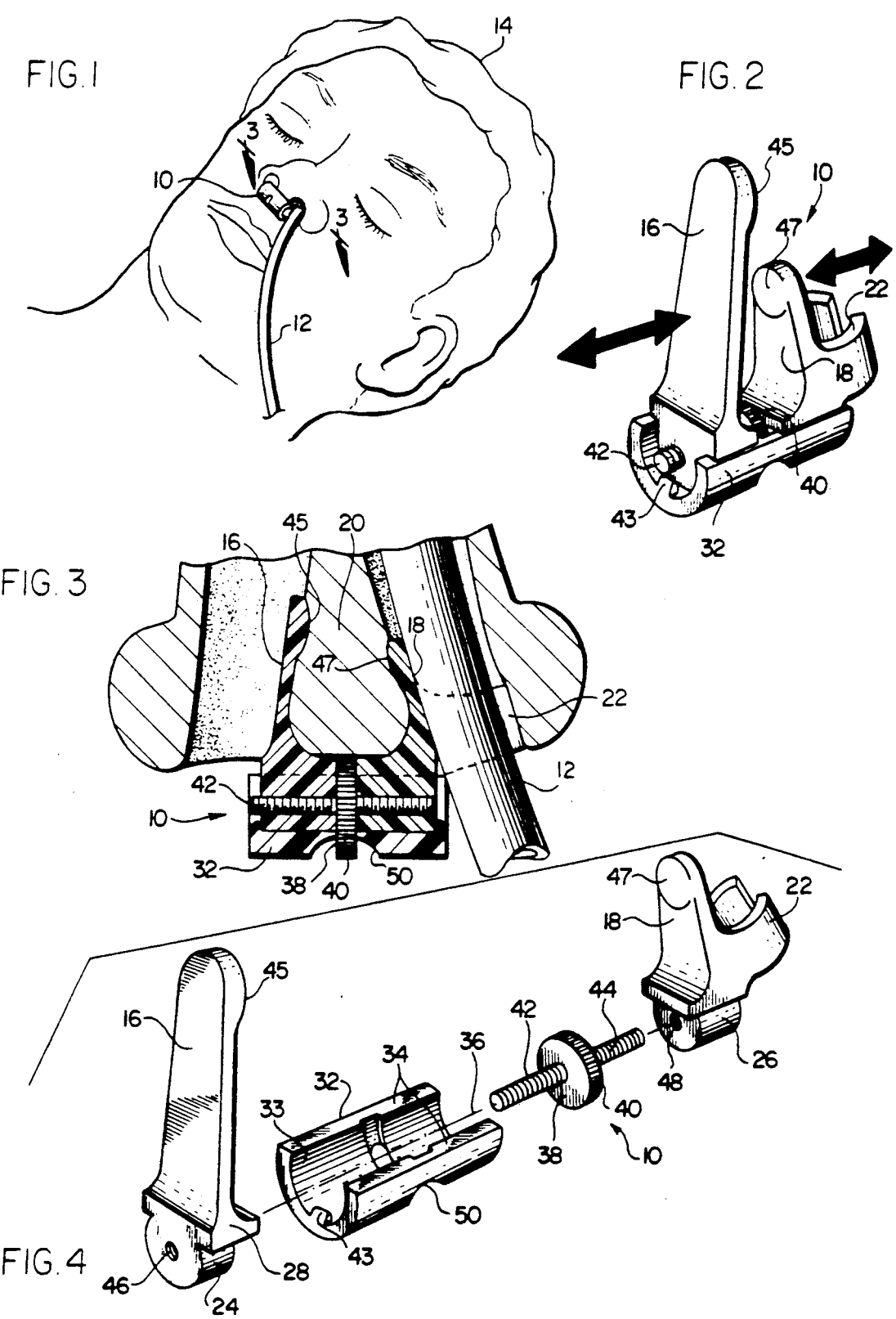

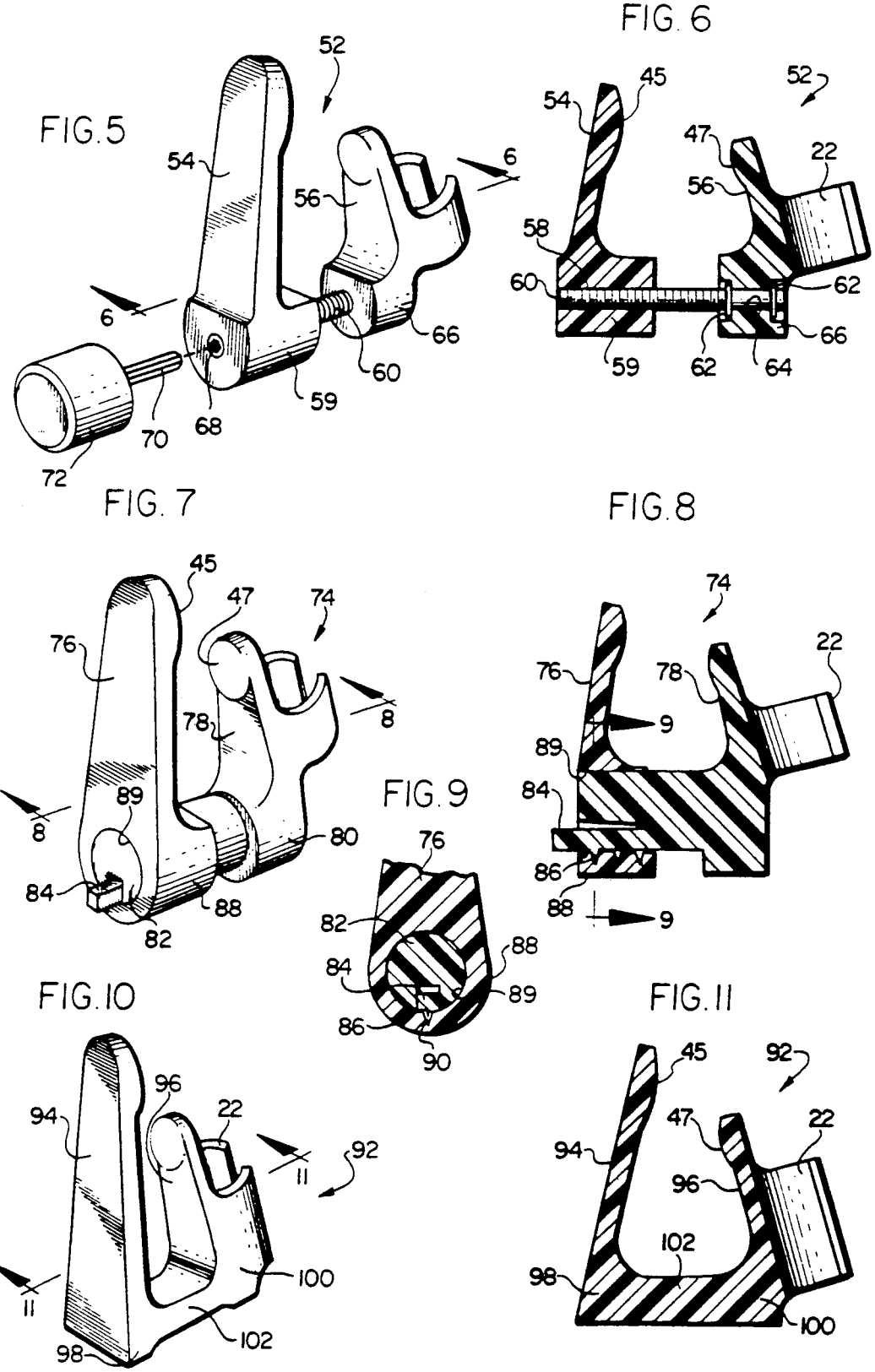

HOLDER FOR MEDICAL TUBING

This invention relates to a holder for medical tubing and in particular to medical tube holding devices for holding nasal gastric tubing in position on a patient.

BACKGROUND OF THE INVENTION

Reference may be made to the following patents of interest U.S. Pat. Nos. 4,336,806; 4,707,906; 4,757,813.

In many hospital situations, during a surgical operation or in post surgery care, there are requirements for various types of medical tubing to be used for supplying fluids to a patient or removing fluids from a patient. Surgical tape is usually applied to the tubing and to the patient or the hospital bed to maintain the tubing in position.

As an example, nasal gastric tubing is often inserted into a patient's nostril with the tubing end reaching to the stomach so as to remove undesired fluids from the patient's stomach. Typically, segments of surgical tape are applied across the tubing and onto a patient's face in order to anchor and hold the tubing in position. In extended care situations the presence of the tape on the patient's face can be irritating and cause discomfiture while also being a potential source of infection by catching food particles, etc. when located near the patient's mouth and chin.

Holding devices for medical tubing have been proposed for maintaining the tubing in a desired position. U.S. Pat. No. 4,336,806 shows a medical tube holder with a backing strip adhesively connected on a back surface to a surgical drape. The backing strip includes magnets on the front surface so that the strip may be folded around a medical tube and the tubing maintained within the holder by the magnetic attraction between the folded backing strip portions.

U.S. Pat. No. 4,707,906 shows a medical tube holder in the form of a metal strip in which the tubing is held by a spring clamping tube portion at one end and wherein the other end is connected to a spring clip which can be fastened to the bed sheets or instruments.

It is now desirable to provide a medical tube holder which can be readily placed into position, particularly when the holder is used for holding nasal gastric tubing inserted into a patient's nostrils and for maintaining the tubing in position.

It is also especially desirable to provide a nasal gastric tube holder which can be utilized with infants as well as adults, and if desired, may be adjustable in size.

SUMMARY OF THE INVENTION

In accordance with the principles of the present invention, there is provided a medical tube holder which is small in size and easily constructed with a minimum of components, and yet which can be used for infants as well as adults.

In a preferred embodiment of the invention, there is provided a medical tube holder for attachment to a patient's nose septum for holding medical tubing, such as a nasal gastric tube inserted into the patient's nose. The tube holder includes opposite upstanding clamp arms adapted to be inserted into the nose on opposite sides of the septum so as to contactingly engage the septum. One of the upstanding nasal clamp arms includes a tube holding portion for receiving and maintaining the medical tubing in position. Connection means intermediate the two spacially disposed clamp arms define and maintain an acute included angle therebetween so that the clamp arms extend inwardly towards each other at their free ends.

In a preferred embodiment of the invention, the connection means between the opposite upstanding clamp arms includes means for adjusting the spacial disposition of the clamp arms. In one embodiment the clamp arms are oppositely threaded and connected together by a thumbscrew. The thumbscrew includes a central adjusting thumbwheel with oppositely threaded screw portions on either side for engagement with a respective, correspondingly threaded clamp arm. A slotted barrel guide member has the thumbscrew mounted in the slot to maintain the axial position of the thumbscrew. Rotating the thumbscrew enables the opposite clamp arms to be guidedly moved within the barrel either simultaneously towards each other or simultaneously apart from each other depending upon the rotational direction of the thumbscrew.

Accordingly, in the preferred embodiment of the invention, the spacial distance between the upstanding nasal clamp arms can be adjusted by means of the thumbscrew to correspond to the size of the patient's septum. After the tubing holder is inserted in position in the nostril, the amount of contact engagement of the upstanding nasal clamp arms with the septum can be adjusted by means of the thumbscrew.

In another embodiment of the invention, only one of the upstanding clamp arms is threaded and the two clamp arms are connected by a threaded adjusting screw. Turning the adjusting screw enables the threaded clamp arm to axially move along the screw threads towards or away from the other non-threaded clamp arm, depending upon the turning direction of the adjusting screw.

In a further embodiment of the invention, the two opposite upstanding nasal clamp arms are connected so as to be slidably adjustable in selected positions with respect to each other. In addition, there is provided a locking pin-detent with several lock detent positions so that the two upstanding clamp arms can be adjusted in slidable position and then located in a selected lock detent position.

In a still further embodiment of the invention, an integral, one-piece medical tube holder is formed with oppositely disposed upstanding nasal clamp arm portions connected by a contiguous connection base portion. The opposite upstanding nasal clamp arm portions are formed with an acute included angle so that the clamp arm portions extend inwardly towards each other at their free ends. The size of the included angle is chosen so that the tube holder may be used for children or adults.

BRIEF DESCRIPTION OF THE DRAWINGS

The features of this invention which are believed to be novel are set forth with particularity in the appended claims. The invention may be best understood by reference to the following description taken in conjunction with the accompanying drawings, in which like reference numerals identify like elements in the several figures and in which:

FIG. 1 is a perspective view illustrating a preferred embodiment of a medical tube holder inserted for engagement with a septum for nasal gastric tubing in accordance with the principles of the present invention;

FIG. 2 is a perspective view illustrating construction details of the embodiment of FIG. 1;

FIG. 3 is a cross-sectional view taken along section lines 3—3 of FIG. 1;

FIG. 4 is an exploded view of the medical tube holder shown in FIG. 1;

FIG. 5 is a perspective view illustrating another embodiment of a medical tube holder in accordance with the present invention;

FIG. 6 is a sectional view taken along section lines 6—6 of FIG. 5;

FIG. 7 is a perspective view illustrating a further embodiment of a medical tube holder according to the invention;

FIG. 8 is a sectional view taken along section lines 8—8 of FIG. 7;

FIG. 9 is a sectional view taken along section lines 9—9 of FIG. 8;

FIG. 10 is a perspective view of a still further embodiment of a medical tube holder in accordance with the present invention; and FIG. 11 is a sectional view taken along section lines 11—11 of FIG. 10.

DETAILED DESCRIPTION

Referring now to the drawings, there are illustrated several embodiments of the present invention which incorporate a pair of opposite upstanding clamp arms adapted for clampingly engaging a body part, bedding or fabric adjacent a patient. One of the upstanding clamp arms includes a tube holding portion for receiving and maintaining medical tubing in position. The primary intended use of a medical tube holder in accordance with the present invention is to be inserted into the nostrils with the upstanding nasal clamp arms engaging the septum for holding and maintaining nasal gastric tubing in position on a patient.

FIGS. 1–4 illustrate the preferred embodiment of a medical tube holder 10 for holding and maintaining the position of a nasal gastric tube 12 with respect to a patient 14. Medical tube holder 10 includes a pair of oppositely disposed upstanding nasal clamp arms 16, 18 formed so that when interconnected there is an acute included angle between the arms which enables insertion into a nostril in clamping contact and engagement with a septum 20. One of the arms such as illustrated arm 18 includes a tube holding portion 22 formed with a split cylindrical section. Tube holding portion 22 is adapted in dimensions so as to enable tubing 12 to be inserted into the split cylinder section while still maintaining the tubing in position.

Each of the upstanding nasal clamp arms 16, 18 includes a respective shoulder 24, 26 and a respective projecting ledge 28, 30. A guide barrel 32 shaped in the form of a cylindrical section includes an inside surface 33 and is adapted in size to enable shoulders 24 and 26 to be slidably disposed therewithin. Projecting ledges 28, 30 extend on each side of the respective arms 16, 18 so as to supportingly rest on guide surfaces 34 provided by a sufficient width of guide barrel 32.

Adjustment in the position of arms 16, 18 along the longitudinal axis 36 of guide barrel 32 is provided by a thumbscrew 38. Thumbscrew 38 is formed with a thumbwheel 40 and a respective threaded screw 42, 44 extending on each side of the thumbwheel. Threaded screw 42 is provided for threadable engagement with a threaded aperture 46 in shoulder 24 of arm 16. Similarly, threaded screw 44 is provided for threadable engagement with a threaded aperture 48 in shoulder 26 of arm 18. Threaded screw 42 and threaded screw 44 are provided with reverse threads so that turning thumbwheel 40 in one direction will move arms 16 and 18 closer together, while turning thumbwheel 40 in the opposite direction will move arms 16 and 18 away from each other.

Guide barrel 32 is provided with a slot 50 through inside surface 33 for receiving thumbwheel 40 and to thereby prevent the thumbscrew from moving along axis 60 as the thumbscrew is turned in either direction. Thus, as can be seen from the exploded view of FIG. 4, the four components of the preferred embodiment of medical tube holder 10 can be readily assembled. Thumbscrew 38 is threadably connected with nasal clamp arms 16, 18 and the combination is snap-inserted into guide barrel 32 with thumbwheel 40 inserted into slot 50. The upstanding nasal clamp arms respective shoulders 24, 26 are in contact with inside surface 33 of the guide barrel so that ledges 28, 30 rest on the guide surfaces 34. Rotation of thumbwheel 40 enables the respective threaded screws 42, 44 to threadably move arms 16, 18 closer together or farther apart. A detent like barrier 43 is located at each end of the guide barrel to prevent inadvertent disassembly of the components during operational adjustment.

As illustrated in the assembled views of FIGS. 2 and 3, the free ends of nasal clamp arms 16, 18 extend inwardly towards each so that there is an acute included angle between the clamp arms sufficient to engage septum 20 in an adjustable clamping action. During rotation of thumbscrew 38 the spacial disposition between the clamp arms is varied but the acute included angle therebetween stays the same.

In using medical tube holder 10, nasal gastric tubing 12 is inserted into tube holder portion 22 and the tubing is inserted into the patient's nostril in accordance with standard medical practice. Tube holder 10 is then moved with respect to tubing 12 so that the nasal clamp arms 16, 18 are inserted into the patient's nostril and on either side of septum 20. Thumbwheel 40 is then rotated in either direction so as to obtain the firm but non-irritating clamping contact engagement of the nasal clamp arms with the septum, aided by opposite clamping pads 45, 47. Removal of holder 10 is easily attained by rotating thumbwheel 40 to move arms 16 and 18 away from each other to disengage them from septum 20, and pulling holder 10 out of the patient's nostril.

Another embodiment of the invention is illustrated in FIGS. 5 and 6. In this embodiment, medical tube holder 52 includes upstanding nasal clamp arms 54, 56. One of the arms, such as arm 54 includes a threaded aperture 58 for engaging a threaded screw 60.

The other arm 56 includes means for connecting the arm to screw 60 so that as the screw 60 rotates, arm 56 is maintained in position and does not move axially along screw 60. Such connecting means include a pair of split rings 62 at opposite ends of an aperture 64 extending through shoulder 66. The split rings are mounted in respective grooves in screw 60. Arm 56 also includes a tube holding portion 22.

One end of threaded screw 60 has a hex shaped end recess 68 for engagement by a similarly hex shaped drive shaft 70 extending from knob 72. As shown in the assembled view of FIG. 6, when connected together the arms 54, 56 form an acute included angle with the free arm ends extending inwardly towards each other similar to that of tube holder 10.

Movement of the arms with respect to each other is provided by inserting drive shaft 70 into hex shaped end 68 of screw 60 and rotating knob 72. Rotating knob 72 in one direction axially moves clamp arm 54 along screw 60 towards stationary arm 56. Rotating knob 72 in the reverse direction moves arm 54 in the opposite direction away from stationary arm 56. The acute included angle between the nasal clamp arms is maintained as the spacial disposition between the arms is varied.

The use of tube holder 52 is similar to tube holder 10. Thus, tubing 12 is inserted into tube holding section 22 and the clamp arms 54, 56 are inserted into the nostril on either side of septum 20. Screw 60 is then rotated with shaft 70 so as to comfortably contactingly engage arms 54 and 56 in a clamping action with septum 20 to maintain tubing 12 in position.

FIGS. 7-9 illustrate another medical tube holder 74 in accordance with the present invention. Tube holder 74 includes upstanding nasal clamp arms 76, 78, with arm 78 including a tube holding cylindrical segment portion 22. Upstanding arm 78 also includes a shoulder 80 with an elongated rod 82 extending from one end of shoulder 80. Rod 82 includes a lever 84 having a pin 86 projecting downwardly from the outer surface of lever 84.

Clamp arm 76 extends upwardly from a shoulder 88, which shoulder includes a bore 89 for receiving the free-end of rod 82 and further includes a series of detents 90 in the bore inner surface. As shown in FIG. 8, locking pin 86 is engaged in a first detent 90 to thereby set the spacial distance between connected arms 76, 78. The distance between the connected arms 76, 78 can be changed by adjusting the position of locking pin 86 in one of the detents 90. For example, with reference to FIG. 8, the distance between arms 76, 78 may be increased by raising lever 84 to disengage locking pin 86 from the first detent 90, axially sliding arm 76 with respect to 78 and releasing lever 84 to locate locking pin 86 in a second or third detent 90. The acute included angle between the nasal clamp arms 76, 78 is maintained as the distance between the arms is varied.

With reference to FIGS. 10 and 11, there is illustrated still another embodiment of the present invention which comprises a medical tube holder 92 which principally differs from the other embodiments heretofore illustrated in that the spacial distance between opposite upstanding nasal clamp arms, 94, 96 is not adjustable. Each of the clamp arms, 94, 96 extend from a respective shoulder 98, 100 interconnected by a contiguous neck portion 102. Arm 96 includes a cylindrical tube holder portion 22.

While the embodiment of FIGS. 10 and 11 is not adjustable, a significant advantage is afforded by the one-piece construction which can reduce the production costs. Integral holder 92 can be provided in at least two different sizes, one for children and one for adults. The difference in the sizes would principally be concerned with having the acute included angle between arms 94 and 96 accommodate a child sized septum in one case and an adult sized septum in another case. Alternatively, a single sized holder 92 may be provided with a suitable choice of an optimum acute included angle between arms 94, 96 to accommodate children and adults and with a suitable choice of material.

It is desirable that a material used to form any of the embodiments illustrated and described in the present invention should be chosen to have characteristics of sufficient strength, resiliency, and lubricity in view of the clamping contact engagement between the upstanding arms of the tube holder on each side of the patient's septum. One material found to be satisfactory is 30/30 polyurethane, although other types of plastic materials and particularly thermosetting polymers may also be utilized.

Tube holder cylindrical segment portion 22 can be adapted to conform to standard sized medical tubing. Alternatively, a conventional bushing adapter can be used for different sized tubing. In such case the bushing outer diameter conforms to the size of the cylindrical tube holder 22 and the bushing inner diameter conforms to the tubing diameter.

The foregoing detailed description has been given for clearness of understanding only, and no unnecessary limitations should be understood therefrom, as modifications will be obvious to those skilled in the art.

What is claimed is:

1. A medical tube holder for attachment to a patient's nose septum for holding medical tubing inserted into the patient's nose, said medical tube holder comprising:
   a first upstanding clamp arm for insertion into the patient's nose and into contact engagement only with one side of the septum substantially along the length of said clamp arm, thereby leaving the nostril substantially unobstructed;
   a second upstanding clamp arm oppositely spacially disposed to said first upstanding clamp arm for insertion into the patient's nose and into contact engagement only with the other side of the septum substantially along the length of said clamp arm,
   said second upstanding clamp arm including a tube holder portion for engageably holding said medical tubing in position; and
   connection means for connecting said oppositely spacially disposed first and second upstanding clamp arms at the end of the septum to define and maintain an acute included angle between said first and second upstanding clamp arms within the patient's nose during contact engagement on opposite sides of the septum.

2. A medical tube holder according to claim 1, wherein said connection means includes adjustment means for varying said spacial disposition of said first and second clamp arms to thereby adjust the respective contact engagement with said septum while maintaining said acute included angle between said first and second clamp arms.

3. A medical tube holder according to claim 2, wherein said adjustment means includes a threaded member threadably engaging at least one of said clamp arms for enabling rotation of said threaded member to vary said spacial disposition of said first and second clamp arms.

4. A medical tube holder according to claim 3, wherein said threaded member threadably engages each of said clamp arms.

5. A medical tube holder according to claim 4, wherein said threaded member includes opposite thread directions on respective member ends.

6. A medical tube holder according to claim 2, wherein said adjustment means includes a rod screw threadably engageable with one of said clamp arms for moving said clamp arm with respect to the other clamp arm during rotation of said rod screw.

7. A medical tube holder according to claim 6, including a rotatable drive member adapted for rotatable engagement with said rod screw.

8. A medical tube holder according to claim 7, wherein said rotatable drive member and threaded rod screw have matching engagement surfaces.

9. A medical tube holder according to claim 2, wherein said adjustment means includes selectable position locking means for selectively adjusting the spacial disposition of said first and second clamp arms and for locking said clamp arms in said selected positions.

10. A medical tube holder according to claim 9, wherein said selectable position locking means includes a lever having at least one locking pin thereon formed on one of said clamp arms and a series of detent positions formed on the other of said clamp arms, wherein adjustably positioning of said clamp arms is provided by engaging the lever to release said locking pin from engagement with a detent and reengaging said locking pin with another selected detent.

11. A medical tube holder according to claim 1, wherein said connection means comprises an integral connection neck portion extending contiguously as an extension from and between said first and second clamp arms, so that said medical tube holder comprises an integral, one-piece unit.

12. A medical tube holder for attachment to a patient's nose septum for holding medical tubing inserted into the patient's nose, said medical tube holder comprising:
a first upstanding clamp arm for insertion into the patient's nose and into contact engagement only with one side of the septum, thereby leaving the nostril substantially unobstructed;
a second upstanding clamp arm oppositely spacially disposed to said first upstanding clamp arm for insertion into the patient's nose and into contact engagement only with the other side of the septum,
said second upstanding clamp arm including a tube holder portion for engageably holding said medical tubing in position; and
connection means for connecting said oppositely spacially disposed first and second upstanding clamp arms to define and maintain an acute included angle therebetween;
said connection means including adjustment means for varying said spacial disposition of said first and second clamp arms to thereby adjust the respective contact engagement with said septum;
said adjustment means including a threaded member having opposite thread directions on respective member ends respectively threadably engaging each of said clamp arms for enabling rotation of said threaded member to vary said spacial disposition of said first and second clamp arms;
said threaded member including a thumbscrew having a thumbwheel with oppositely threaded screw members on respective sides of said thumbwheel for moving said clamp arms simultaneously towards each other or simultaneously away from each other in response to the rotational direction of said thumbwheel.

13. A medical tube holder according to claim 12, wherein said connection means includes a guide member, said first and second upstanding clamp arms slidably mounted in said guide member for slidable movement in response to rotation of said thumbwheel.

14. A medical tube holder according to claim 13, wherein said guide member includes a slot for mounting said thumbwheel and preventing axial movement of said thumbscrew during operation of said thumbwheel.

15. A medical tube holder according to claim 14, wherein said clamp arms each includes a shoulder portion adapted for slidable movement within said guide member during operation of said thumbscrew.

16. A medical tube holder according to claim 15, wherein said guide member comprises a cylindrical segment having a width sufficient to form a guide surface.

17. A medical tube holder according to claim 16, wherein said clamp arms include an overhanging ledge portion immediately adjacent said shoulder portion, said ledge portion slidably mountable on said guide surface.

18. A medical tube holder for attachment to a patient's nose septum for holding medical tubing inserted into the patient's nose, said medical tube holder comprising:
a first upstanding clamp arm for insertion into the patient's nose and into contact engagement only with one side of the septum substantially along the length of said clamp arm, thereby leaving the nostril substantially unobstructed;
a second upstanding clamp arm oppositely spacially disposed to said first upstanding clamp arm for insertion into the patient's nose and into contact engagement only with the other side of the septum substantially along the length of said clamp arm,
said second upstanding clamp arm including a tube holder portion for engageably holding said medical tubing in position; and
adjustable positioning means for adjustably positioning the spacing between said first and second nasal clamp arms to adjust the respective contact engagement of said first and second nasal clamp arms with said septum and thereby adjust for variable sized septums.

19. A medical tube holder for attachment to a patient's nose septum for holding medical tubing inserted into the patient's nose, said medical tube holder comprising:
a first upstanding clamp arm for insertion into the patient's nose and into contact engagement only with one side of the septum substantially along the length of said clamp arm, thereby leaving the nostril substantially unobstructed;
a second upstanding clamp arm oppositely spacially disposed to said first upstanding clamp arm for insertion into the patient's nose and into contact engagement only with the other side of the septum substantially along the length of said clamp arm;
said second upstanding clamp arm including a tube holder portion for engageably holding said medical tubing in position; and
a continuously adjustable connector member intermediately connected between said first and second nasal clamp arms for selected continuous adjustment of the positions of said first and second nasal clamp arms with respect to each other so as to adjustably vary the clamping contact engagement of said medical tube holder on the septum and thereby adjust for variably sized septums.

20. A medical tube holder according to claim 19, wherein said continuously adjustable connector member includes a thumbscrew enabling threadable adjustment in the relative positions of said first and second nasal clamp arms.

* * * * *